US007772206B2

(12) United States Patent
Wood et al.

(10) Patent No.: US 7,772,206 B2
(45) Date of Patent: Aug. 10, 2010

(54) METHODS AND COMPOSITIONS FOR THE TREATMENT OF AUTOIMMUNE DISORDERS USING CLOFARABINE

(75) Inventors: Christopher B. Wood, Stoke Poges (GB); Stuart W. Smith, Stirlingshire (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 12/394,872

(22) Filed: Feb. 27, 2009

(65) Prior Publication Data

US 2009/0155211 A1 Jun. 18, 2009

Related U.S. Application Data

(62) Division of application No. 10/529,519, filed as application No. PCT/US03/30409 on Sep. 25, 2003, now abandoned.

(60) Provisional application No. 60/414,687, filed on Sep. 27, 2002.

(51) Int. Cl.
*A01N 43/04* (2006.01)
*A61K 31/70* (2006.01)
(52) U.S. Cl. .............. 514/46; 514/43; 514/45; 514/47; 514/48
(58) Field of Classification Search .............. None
See application file for complete search history.

(56) References Cited

U.S. PATENT DOCUMENTS

| | | |
|---|---|---|
| 3,536,809 A | 10/1970 | Dingivan |
| 3,598,123 A | 8/1971 | Zaffaroni |
| 3,845,770 A | 11/1974 | Theeuwes |
| 3,916,899 A | 11/1975 | Theeuwes |
| 3,928,319 A | 12/1975 | Jenkins |
| 4,008,719 A | 2/1977 | Theeuwes |
| 4,145,531 A | 3/1979 | Eckstein |
| 4,188,378 A | 2/1980 | Montgomery |
| 4,210,745 A | 7/1980 | Montgomery |
| 4,357,324 A | 11/1982 | Montgomery |
| 4,751,221 A | 6/1988 | Watanabe |
| 4,765,539 A | 8/1988 | Noakes |
| 4,918,179 A | 4/1990 | Watanabe |
| 4,962,885 A | 10/1990 | Coffee |
| 5,059,595 A | 10/1991 | LeGrazie |
| 5,073,543 A | 12/1991 | Marshall |
| 5,106,837 A | 4/1992 | Carson |
| 5,112,598 A | 5/1992 | Biesalski |
| 5,120,548 A | 6/1992 | McClelland |
| 5,304,514 A | 4/1994 | Nishibe |
| 5,310,732 A | 5/1994 | Carson |
| 5,354,556 A | 10/1994 | Sparks |
| 5,384,310 A | 1/1995 | Montgomery |
| 5,506,213 A | 4/1996 | Carson |
| 5,506,214 A * | 4/1996 | Beutler ................ 514/46 |
| 5,556,611 A | 9/1996 | Biesalski |
| 5,591,767 A | 1/1997 | Mohr |
| 5,639,476 A | 6/1997 | Oshlack |
| 5,661,136 A | 8/1997 | Montgomery |
| 5,674,533 A | 10/1997 | Santus |
| 5,733,566 A | 3/1998 | Lewis |
| 5,950,619 A | 9/1999 | van der Linden |
| 5,954,047 A | 9/1999 | Armer |
| 5,970,974 A | 10/1999 | van der Linden |
| 2002/0168360 A1 | 11/2002 | Dingivan |

FOREIGN PATENT DOCUMENTS

| | | |
|---|---|---|
| EP | 0364559 | 9/1995 |
| WO | WO 89/08658 | * 3/1989 |

OTHER PUBLICATIONS

Mackay et al. N. Engl. J. Med. (2001), vol. 345, pp. 340-350.*
Iiyas et al. J. Am. Acad. Dermatol. (1999), vol. 41, pp. 316-318.*
Huang, P., Phosphorolytic Cleavage of 2-Fluoroadenine From 9-B-D-Arabinofuranosyl-2-fluoroadenine by *Escherichia coli*, Biochemical Pharmacology, 36, No. 18, pp. 3945-2950, 1987.
Struck, R., Identification of Metabolites of 9-B-D-Arabinofuranosyl-2-fluoroadenine, an antitumor and antiviral agent, Biochemical Pharmacology, vol. 31, No. 11, pp. 1975-1978, 1982.
Haertle, T., Metabolism and Anti-human Immunodeficiency Virus-1 Activity of 2-Halo-2',3'-dideoxyadenosine Derivatives, The Journal of Biological Chemistry, vol. 263, No. 12, 5870-5875, 1988.
Secrist, J., Synthesis and Biological Evaluations of Certain 2-Halo-2'-Substituted Derivatives of 9-B-D-Arabinofuranosyladenine, J. Med. Chem, 1988,3 1-405-410.
Montgomery, J., 9-(2-Deoxy-2-fluoro-B-D-arabinofuranosyl)guanine: A Metabolically Stable Cytotoxic Analogue of 2'-Deoxyguanosine, J. Med. Chem, 1986, 29, 2389-2392.
Carson, Oral Antilymphocyte Activity and Inductions . . . , Proc Nat Acad Sci, vol. 89, No. 7, 1992, pp. 2970-2974.
Dahl, Inhaled Isotretinoin (13-cis Retinoic Acid) . . . , Clinical Cancer Research, vol. 6, 3015-2034 Aug. 2000.

* cited by examiner

*Primary Examiner*—Patrick T Lewis
(74) *Attorney, Agent, or Firm*—Christopher J. Verni

(57) ABSTRACT

This invention relates to methods of treating or preventing an autoimmune disorder comprising the administration of clofarabine or a pharmaceutically acceptable salt, hydrate, solvate, clathrate, prodrug or metabolite thereof to a patient in need of such treatment. The invention further relates to methods of treating or preventing an autoimmune disorder comprising the administration of clofarabine or a pharmaceutically acceptable salt, hydrate, solvate, clathrate, prodrug or metabolite thereof and an additional therapeutic agent to a patient in need of such treatment.

20 Claims, No Drawings

METHODS AND COMPOSITIONS FOR THE TREATMENT OF AUTOIMMUNE DISORDERS USING CLOFARABINE

This application is a divisional of U.S. application Ser. No. 10/529,519 filed Aug. 24, 2005, now abandoned, which is a National Stage Application filed under 35 U.S.C. §371 of PCT/US03/30409 filed Sep. 25, 2003, which in turn claims the benefit of U.S. Application No. 60/414,687 filed Sep. 27, 2002, the contents of all of which are hereby incorporated herein by reference for all purposes.

1. FIELD OF THE INVENTION

This invention relates to pharmaceutical compositions, dosage forms and dosage regimens utilizing clofarabine. This invention also relates to methods of treating autoimmune disorders, and to methods for dosing clofarabine, each of these methods also encompasses reducing or avoiding undesired effects associated with conventional treatment of autoimmune disorders.

2. BACKGROUND OF THE INVENTION

2.1 Autoimmune Disorders

The immune system is a complicated network of cells and cell components that defend the body and eliminate infections caused by bacteria, viruses, and other invading microbes. Autoimmune disorders, however, cause the immune system to mistakenly attack the cells, tissues, and organs of a patient's own body.

There are many different autoimmune diseases, and they can each affect the body in different ways. Autoimmune disorders can target specific organs and tissues in the body, e.g., the brain, as in Multiple Sclerosis, or the gastrointestinal system as in Crohn's disease. In other cases, autoimmune disorders can affect a variety of tissues in the same patient or from patient to patient. Additionally, autoimmune disorders can have permanent effects on the body, such as in the causal role of Type I, insulin dependent diabetes.

Some autoimmune diseases are known to begin or worsen with certain triggers such as viral infections. It is important to be aware of the factors that can be avoided to help prevent or minimize the amount of damage from the autoimmune disease. Other less understood influences affecting the immune system and the course of autoimmune diseases include aging, chronic stress, hormones and pregnancy.

Traditional medications slow or suppress the immune system response in an attempt to stop the inflammation involved in the autoimmune attack. For example, medication can slow or stop the immune system's destruction of the kidneys or joints. These drugs include corticosteroids (prednisone), methotrexate, cyclophosphamide, azathioprine, and cyclosporins. Unfortunately, these medications also suppress the ability of the immune system to fight infection and have other potentially serious side effects.

A current goal in caring for patients with autoimmune diseases is to find treatments that produce remissions with fewer side effects.

2.2 Clofarabine

Purine nucleosides have been previously reported as useful for the treatment of cancers. An exemplary class of purine nucleosides and their potential use in anti-cancer therapy is disclosed in U.S. Pat. Nos. 4,751,221 and 4,918,179. Subsequently, the specific nucleosides fludarabine and clofarabine and their proposed utility as cytotoxic compounds were described in U.S. Pat. Nos. 5,304,514; 5,384,310 and 5,661,136.

Clofarabine is an adenosine nucleoside analogue which is chemically named 2 Chloro 9 (2 deoxy 2 fluoro β D arabinofuranosyl)adenine [CL-F-Ara-A]. Shortnacy Fowler A T, Tiwari K N, Montgomery J A, et al. Synthesis and biological activity of 4' C hydroxymethyl 2' fluoro D arabinofuranosylpurine nucleosides. Nucleosides Nucleotides Nucleic Acids 20(8):1583 98, 2001.

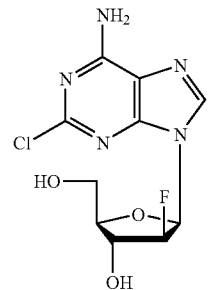

Clofarabine appears to have multiple mechanisms of action against cancer, including inhibiting both DNA polymerases and ribonucleotide reductase and inducing apoptosis. It also appears to be effective against certain cancers through a unique additional mechanism, whereby it directly damages the mitochondria in cancer cells and induces apoptosis (Genini D, Adachi S, Chao Q, et al. *Blood* 2000 96: 3537).

Clofarabine is also known by the tradename CLOFAREX, and is being developed for the acute treatment of myelogenous leukemia in adults, for acute lymphocytic leukemia in children and for the treatment of advanced solid tumors in adults. Johnson S A. Nucleoside analogues in the treatment of hematological malignancies. *Expert Opin Pharmacother* 2(6):929-43, 2001.

Recently, certain nucleoside analogs have been reported to have potential utility at low doses (0.04 to about 0.20 mg/kg/day) in treating autohemyltic anemia (U.S. Pat. No. 5,106,837); rheumatoid arthritis (U.S. Pat. No. 5,310,732); and inflammatory Bowel Disease (U.S. Pat. No. 5,506,213). Furthermore, a class of nucleoside analogs have been reported to have potential utility in the treatment of multiple sclerosis at doses from about 0.04 to about 0.20 mg/kg per day (U.S. Pat. No. 5,506,214).

Clofarabine is an interesting anticancer drug candidate. However, all of the potential uses for clofarabine have thus far remained unexplored or undeveloped. Further, there remains a need for high dosage compositions. Also, as discussed above, treatments for autoimmune disorders are needed. Finally, dosing regimens, particularly for the use of clofarabine in the treatment of diseases other than cancer are needed.

3. SUMMARY OF THE INVENTION

This invention encompasses compositions comprising, and methods of using, clofarabine, and pharmaceutically acceptable salts, stereoisomers, solvates, hydrates and clathrates thereof.

A first embodiment of the invention encompasses a method of treating, preventing or managing an autoimmune disorder which comprises administering to a patient in need of such treatment a therapeutically or prophylactively effective amount of clofarabine or a pharmaceutically acceptable salt, solvate, hydrate, or clathrate thereof. In a specific embodiment of the invention, the autoimmune disorder is a disorder of the nervous system, the blood, the gastrointestinal system, the endocrine glands, the skin, the musculoskeletal system, the connective tissue or combinations thereof. Significantly, the invention encompasses novel doses and dosing regimens for treating autoimmune disorders. In particular, doses higher than those previously contemplated in the art are used chronically or periodically and in cycling therapy to treat or prevent autoimmune disorders. A preferred embodiment is to treat multiple sclerosis with doses higher than previously contemplated in the art.

In a preferred embodiment, the invention encompasses the treatment, prevention or management of certain specific autoimmune disorders including, but not limited to, Alopecia Areata, Ankylosing Spondylitis, Antiphospholipid Syndrome, Autoimmune Addison's Disease, Autoimmune Hemolytic Anemia, Autoimmune Hepatitis, Autoimmune Uveitis, Autoimmune Oophoritis, Autoimmune Orchitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, Dermatitis Herpetiformis, Essential Mixed Cryoglobulinemia, Fibromyalgia-Fibromyositis, Graves' Disease, Guillain-Barré, Hashimoto's Thyroiditis, Idiopathic Pulmonary Fibrosis, Idiopathic Thrombocytopenia Purpura (ITP), IgA Nephropathy, Insulin dependent Diabetes, Immune Mediated Diabetes, Juvenile Arthritis, Lichen Planus, Ménière's Disease, Mixed Connective Tissue Disease, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammag-lobulinemia, Primary Biliary Cirrhosis, Psoriasis, Raynaud's Phenomenon, Reiter's Syndrome, Rheumatic Fever, Sarcoidosis, Scleroderma, Sjögren's Syndrome, Stiff-Man Syndrome, Takayasu Arteritis, Temporal Arteritis, Giant Cell Arteritis, Ulcerative Colitis, Uveitis, Vasculitis, Vitiligo or Wegener's Granulomatosis.

In a preferred embodiment, the multiple sclerosis is relapsing-remitting multiple sclerosis or secondary progressive multiple sclerosis.

In another preferred embodiment, the patient to be treated is a human, including adults, adolescents, children, and infants.

A second embodiment of the invention encompasses a method of treating, preventing or managing an autoimmune disorder comprising administering to a patient in need of such treatment a therapeutically or prophylactively effective amount of clofarabine or a pharmaceutically acceptable salt, solvate, hydrate, or clathrate thereof and an additional therapeutic agent. In a preferred embodiment, the additional therapeutic agent is an antibiotic, an antiemetic agent, an antidepressant, and antifungal agent, an antiinflammatory agent, an antiviral agent, an immunomodulatory agent, a β-Interferon, an alkylating agent, a hormone or a cytokine.

A third embodiment of the invention encompasses a method of reducing or avoiding adverse effects of traditional therapies for autoimmune disorders which comprises administering to a patient in need of such relief a therapeutically or prophylactively effective amount of clofarabine or a pharmaceutically acceptable salt, solvate, hydrate, or clathrate thereof. Examples of adverse effects include, but are not limited to, nausea, reversible kidney dysfunction, depression, herpes zoster infection and skin rash.

Similarly, the dosing regimens avoid or reduce the side or adverse or unwanted effects associated with the administration of purine nucleoside analogues such as fludarabine and cladribine.

3.1 Definitions

As used herein, the term "patient" means an animal (e.g., cow, horse, sheep, pig, chicken, turkey, quail, cat, dog, mouse, rat, rabbit, guinea pig, etc.), preferably a mammal such as a non-primate and a primate (e.g., monkey and human), most preferably a human. In certain embodiments, the patient is an infant, child, adolescent or adult.

As used herein, a "therapeutically effective amount" refers to that amount of the compound of the invention or other active ingredient sufficient to provide a therapeutic benefit in the treatment or management of the disease or to delay or minimize symptoms associated with the disease. Further, a therapeutically effective amount with respect to a compound of the invention means that amount of therapeutic agent alone, or in combination with other therapies, that provides a therapeutic benefit in the treatment or management of the disease. Used in connection with an amount of a compound of the invention, the term can encompass an amount that improves overall therapy, reduces or avoids symptoms or causes of disease, or enhances the therapeutic efficacy of or synergies with another therapeutic agent.

As used herein, a "prophylactically effective amount" refers to that amount of a compound of the invention or other active ingredient sufficient to result in the prevention, recurrence or spread of the disease. A prophylactically effective amount may refer to the amount sufficient to prevent initial disease or the recurrence or spread of the disease or the occurrence of the disease in a patient, including but not limited to those predisposed to the disease. A prophylactically effective amount may also refer to the amount that provides a prophylactic benefit in the prevention of the disease. Further, a prophylactically effective amount with respect to a compound of the invention means that amount alone, or in combination with other agents, that provides a prophylactic benefit in the prevention of the disease. Used in connection with an amount of a compound of the invention, the term can encompass an amount that improves overall prophylaxis or enhances the prophylactic efficacy of or synergies with another prophylactic agent.

As used herein, a "therapeutic protocol" refers to a regimen of timing and dosing of one or more therapeutic agents.

As used herein, a "prophylactic protocol" refers to a regimen of timing and dosing of one or more prophylactic agents.

A used herein, a "protocol" includes dosing schedules and dosing regimens. As used herein, "in combination" refers to the use of more than one prophylactic and/or therapeutic agents.

As used herein, the terms "manage", "managing" and "management" refer to the beneficial effects that a subject derives from a prophylactic or therapeutic agent, which does not result in a cure of the disease. In certain embodiments, a subject is administered one or more prophylactic or therapeutic agents to "manage" a disease so as to prevent the progression or worsening of the disease.

As used herein, the terms "prevent", "preventing" and "prevention" refer to the prevention of the onset recurrence, spread or of the disease in a subject resulting from the administration of a prophylactic or therapeutic agent.

As used herein, the terms "treat", "treating" and "treatment" refer to the eradication or amelioration of the disease or symptoms associated with the disease. In certain embodiments, such terms refer to minimizing the spread or worsening of the disease resulting from the administration of one or more prophylactic or therapeutic agents to a subject with such a disease.

As used herein, the term "pharmaceutically acceptable salts" refer to salts prepared from pharmaceutically acceptable non-toxic acids or bases including inorganic acids and bases and organic acids and bases. Suitable pharmaceutically acceptable base addition salts for the compound of the present invention include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts.

As used herein and unless otherwise indicated, the term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "metabolite" means the product of metabolism of a compound of the invention, e.g., a metabolite is a compound formed by hydrolysis, oxidation, or other in vivo reaction, particularly in the liver. In other words, the invention contemplates the synthesis and administration of compounds that are in vivo metabolites of clofarabine. Examples of metabolites include, but are not limited to, derivatives of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, metabolites of compounds of the invention are monophosphates, diphosphates and triphosphates, more preferably triphosphates.

As used herein and unless otherwise indicated, the term "optically pure" or "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. Furthermore, the sugar moiety of the nucleoside analog can exist in either the D or L forms of the sugar. As such, for example, a stereomerically pure composition of a D compound will be substantially free of the L form of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "enantiomerically pure" means a stereomerically pure composition of a compound having one chiral center.

As used herein, the term "connective tissue" means tissue in the body that maintains the form of the body and its organs and provides cohesion and internal support, such as bone, ligaments, tendons, cartilage, adipose tissue, and aponeuroses.

4. DETAILED DESCRIPTION OF THE INVENTION

4.1 The Compound of the Invention Clofarabine

The invention encompasses the use of clofarabine in the methods, compositions and dosage forms described herein. It should be recognized by one of skill in the art that the invention encompasses pharmaceutically acceptable salts, hydrates, clathrates, polymorphs, prodrugs, and stereoisomers of clofarabine, including both the D and L isomers of the sugar moeity as well as metabolites. Clofarabine is readily prepared using the methods in U.S. Pat. Nos. 5,034,518, 5,384,310, and 5,661,136 which are incorporated herein by reference. Alternatively, clofarabine is commercially available and can be purchased.

Stereochemically pure compounds can be obtained from the racemic compound by techniques known in the art.

Examples include, but are not limited to, the formation of chiral salts and the use of chiral or high performance liquid chromatography "HPLC" and the formation and crystallization of chiral salts. See, e.g., Jacques, J., et al., Enantiomers, Racemates and Resolutions (Wiley-Interscience, New York, 1981); Wilen, S. H., et al., Tetrahedron 33:2725 (1977); Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

Prodrugs and metabolites of Clofarabine can be readily produced by methods well known in the art such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh). Particular metabolites of clofarabine encompassed by the invention are clofarabine phosphate, clofarabine diphosphate and clofarabine triphosphate. In a preferred embodiment of the invention, the metabolite is clofarabine triphosphate.

4.2 Methods of Use

The invention encompasses methods of treating, preventing or managing autoimmune diseases or disorders in a patient which comprise administering to a patient in need of such treatment or prevention a therapeutically effective amount of clofarabine, or a pharmaceutically acceptable prodrug, stereoisomer, salt, solvate, hydrate, or clathrate thereof.

Autoimmune disorders within the scope of the methods of the invention are those which target the nervous system, the blood, the gastrointestinal system, the endocrine glands, the skin, the musculoskeletal system, the connective tissue or combinations thereof. Specific autoimmune diseases or disorders within the scope of the methods of the invention are: Alopecia Areata, Ankylosing Spondylitis, Antiphospholipid Syndrome, Autoimmune Addison's Disease, Autoimmune Hemolytic Anemia, Autoimmune Hepatitis, Autoimmune Uveitis, Autoimmune Oophoritis, Autoimmune Orchitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, Dermatitis Herpetiformis, Essential Mixed Cryoglobulinemia, Fibromyalgia-Fibromyositis, Graves' Disease, Guillain-Barré, Hashimoto's Thyroiditis, Idiopathic Pulmonary Fibrosis, Idiopathic Thrombocytopenia Purpura (ITP), IgA Nephropathy, Insulin dependent Diabetes, Immune Mediated Diabetes, Juvenile Arthritis, Lichen Planus, Ménière's Disease, Mixed Connective Tissue Disease, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammag-lobulinemia, Primary Biliary Cirrhosis, Psoriasis, Raynaud's Phenomenon, Reiter's Syndrome, Rheumatic Fever, Sarcoidosis, Scleroderma, Sjögren's Syndrome, Stiff-Man Syndrome, Takayasu Arteritis, Temporal Arteritis, Giant Cell Arteritis, Ulcerative Colitis, Uveitis, Vasculitis, Vitiligo or Wegener's Granulomatosis.

In other embodiments, diseases to be treated or prevented by administering to a patient in need thereof an effective amount of clofarabine include Alopecia Areata, Ankylosing Spondylitis, Antiphospholipid Syndrome, Autoimmune Addison's Disease, Autoimmune Hemolytic Anemia, Autoimmune Hepatitis, Autoimmune Uveitis, Autoimmune Oophoritis, Autoimmune Orchitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, Dermatitis Herpetiformis, Essential Mixed Cryoglobulinemia, Fibromyalgia-Fibromyositis, Graves' Disease, Guillain-Barré, Hashimoto's Thyroiditis, Idiopathic Pulmonary Fibrosis, Idiopathic Thrombocytopenia Purpura (ITP), IgA Nephropathy, Insulin dependent Diabetes, Immune Mediated Diabetes, Juvenile Arthritis, Lichen Planus, Ménière's Disease, Mixed Connective Tissue Disease, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammag-lobulinemia, Primary Biliary Cirrhosis, Psoriasis, Raynaud's Phenomenon, Reiter's Syndrome, Rheumatic Fever, Sarcoidosis, Scleroderma, Sjögren's Syndrome, Stiff-Man Syndrome, Takayasu Arteritis, Temporal Arteritis, Giant Cell Arteritis, Ulcerative Colitis, Uveitis, Vasculitis, Vitiligo or Wegener's Granulomatosis.

In preferred embodiments of the invention, the multiple sclerosis is relapsing-remitting multiple sclerosis or secondary progressive multiple sclerosis.

Specific methods of the invention further comprise the administration of an additional therapeutic agent (i.e. a therapeutic agent other than a compound of the invention) In certain embodiments of the present invention, the compounds of the invention can be used in combination with at least one other therapeutic agent. Therapeutic agents include, but are not limited to antibiotics, antiemetic agents, antidepressants, and antifungal agents, antiinflammatory agents, antiviral agents, immunomodulatory agents, β-interferons, alykylating agents, hormones or cytokines.

In certain embodiments, clofarabine can be administered or formulated in combination with antibiotics. In certain embodiments, the antibiotic is a macrolide (e.g., tobramycin (Tobi®)), a cephalosporin (e.g., cephalexin (Keflex®), cephradine (Velosef®), cefuroxime (Ceftin®)), cefprozil (Cefzil®)), cefaclor (Ceclor®), cefixime (Suprax®) or cefadroxil (Duricef®)), a clarithromycin (e.g. clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), macrolides (e.g., azithromycin, carbomycin, clarithomycin, dirithromycin, erythromycin, and erylromycin acistrate), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, ciprofloxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

In certain embodiments, clofarabine can be administered or formulated in combination with an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

In certain embodiments, clofarabine can be administered or formulated in combination with an antidepressant. Suitable antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpirde, tandospirone, thozalinone, tofenacin, toloxatone, tranylcypromine, L-tryptophan, venlafaxine, viloxazine, and zimeldine.

In certain embodiments, clofarabine can be administered or formulated in combination with an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofuldin.

In certain embodiments, clofarabine can be administered or formulated in combination with an antiinflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; and other anti-inflammatory agents including, but not limited to, methotrexate, colchicine, allopurinol, probenecid, sulfinpyrazone and benzbromarone.

In certain embodiments, clofarabine can be administered or formulated in combination with an antiviral agent. Useful antiviral agents include, but are not limited to, nucleoside analogs, such as zidovudine, acyclovir, gangcyclovir, vidarabine, idoxuridine, trifluridine, and ribavirin, as well as foscarnet, amantadine, rimantadine, saquinavir, indinavir, ritonavir, and the alpha-interferons.

Examples of immunomodulatory agents include, but are not limited to, methotrexate, leflunomide, cyclophosphamide, cyclosporine A, macrolide antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators.peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators.

Examples of T cell receptor modulators include, but are not limited to, anti-T cell receptor antibodies (e.g., anti-CD4 antibodies (e.g., cM-T412 (Boeringer), IDEC-CE9.1 (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), and anti-B7 antibodies (e.g., IDEC-114) (IDEC))) and CTLA4-immunoglobulin. In a specific embodiment, a T cell receptor modulator is a CD2 antagonist. In other embodiments, a T cell receptor modulator is not a CD2 antagonist. In another specific embodiment, a T cell receptor modulator is a CD2 binding molecule, preferably MEDI-507. In other embodiments, a T cell receptor modulator is not a CD2 binding molecule.

Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, TNF-β, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti- IL-8 antibodies (e.g., ABX-IL-8 (Abgenix)), and anti-IL-12 antibodies). In a specific embodiment, a cytokine receptor modulator is IL-4, IL-10, or a fragment thereof. In another embodiment, a cytokine receptor modulator is an anti-IL-1β antibody, anti-IL-6 antibody, anti-IL-12 receptor antibody, or anti-TNF-α antibody. In another embodiment, a cytokine receptor modulator is the extracellular domain of a TNF-α receptor or a fragment thereof. In certain embodiments, a cytokine receptor modulator is not a TNF-α antagonist.

In a preferred embodiment, proteins, polypeptides or peptides (including antibodies) that are utilized as immunomodulatory agents are derived from the same species as the recipient of the proteins, polypeptides or peptides so as to reduce the likelihood of an immune response to those proteins, polypeptides or peptides. In another preferred embodiment, when the subject is a human, the proteins, polypeptides, or peptides that are utilized as immunomodulatory agents are human or humanized.

Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSP), granulocyte colony stimulating factor (G-CSF), macrophage colony stimulating factor (M-CSF), prolactin, and interferon (IFN), e.g., IFN-alpha, and IFN-gamma).

Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins.

Examples of β-interferons include, but are not limited to, interferon beta-1a and interferon beta1-b.

Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

Clofarabine and the other therapeutics agent can act additively or, more preferably, synergistically. In a preferred embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent.

4.3 Doses and Dosage Forms

The magnitude of a prophylactic or therapeutic dose of clofarabine or a pharmaceutically acceptable salt, solvate, hydrate, clathrate, prodrug, metabolite or stereoisomer thereof in the acute or chronic management of a disease or condition will vary, however, with the nature and severity of the disease or condition, and the route by which the active ingredient is administered. The dose, and perhaps the dose frequency, will also vary according to the disease to be treated, the age, body weight, and response of the individual patient. Suitable dosing regimens can be readily selected by those skilled in the art with due consideration of such factors. In one embodiment, the dose of clofarabine is greater than about 0.04 mg/kg/day, preferably greater than 0.20 mg/kg/day, most preferably greater than 1 mg/kg/day. In general, the recommended daily dose range for the conditions described herein lie within the range of from about 1.25 mg/kg to about 80 mg/kg per day, given as a single once-a-day dose, preferably as divided doses throughout a day. Additionally, the recommended daily dose ran can be administered in cycles as single agents or in combination with other therapeutic agents. In one embodiment, the daily dose is administered in a single dose or in equally divided doses. Specifically, a daily dose range should be from about 5 mg/kg to about 75 mg/kg per day, more specifically, between about 20 mg/kg and about 60 mg/kg per day, most specifically between about 40 mg/kg and 50 mg/kg per day. In managing the patient, the therapy should be initiated at a lower dose, perhaps about 1.25 mg/kg to about 25 mg/kg per day, and increased if necessary up to about 40 mg/kg to about 50 mg/kg per day as either a single dose or divided doses, depending on the patient's global response. In the treatment of chronic diseases and disorders, the recommended daily dose range for the conditions described herein lie within the range of from about 1.25 mg/kg to about 10 mg/kg per day, given as a single once-a-day dose, preferably as divided doses throughout a day. Specifically, a daily dose range for chronic conditions should be from about 2 mg/kg to about 6 mg/kg per day, more specifically, between about 4 mg/kg and about 5 mg/kg per day.

It may be necessary to use dosages of the active ingredient outside the ranges disclosed herein in some cases, as will be apparent to those of ordinary skill in the art, but the dosage should not fall below 1.0 mg/kg/day. The maximum tolerated doses of clofarabine is approximately 80 mg/kg per day. Furthermore, it is noted that the clinician or treating physician will know how and when to interrupt, adjust, or terminate therapy in conjunction with individual patient response.

Different therapeutically effective amounts may be applicable for different diseases and conditions, as will be readily known by those of ordinary skill in the art. Similarly, amounts sufficient to treat or prevent such diseases, but insufficient to cause, or sufficient to reduce, adverse effects associated with conventional therapies are also encompassed by the above described dosage amounts and dose frequency schedules.

In a preferred embodiment, the invention encompasses a method for treating, preventing, or managing multiple sclerosis utilizing doses higher than 1 mg/kg per day, preferably higher than 1.25 mg/kg per day.

4.4 Pharmaceutical Compositions

Pharmaceutical compositions and single unit dosage forms comprising clofarabine, or a pharmaceutically acceptable polymorph, prodrug, salt, stereoisomer, solvate, hydrate, or clathrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration.

Pharmaceutical compositions and dosage forms of the invention comprise clofarabine, or a pharmaceutically acceptable prodrug, polymorph, salt, stereoisomer, solvate, hydrate, or clathrate thereof. Pharmaceutical compositions and dosage forms of the invention typically also comprise one or more pharmaceutically acceptable excipients.

A particular pharmaceutical composition encompassed by this embodiment comprises clofarabine, or a pharmaceutically acceptable polymorph, prodrug, salt, solvate, hydrate, or clathrate thereof, and at least one additional therapeutic agent. Examples of additional therapeutic agents include, but are not limited to, those listed above in section 4.2.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., fens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g. vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise clofarabine, or a pharmaceutically acceptable salt, solvate, clathrate, hydrate, polymorph or prodrug thereof lie within the range of from 5 mg/kg to about 75 mg/kg per day, more specifically, between about 20 mg/kg and about 60 mg/kg per day, most specifically between about 40 mg/kg and 50 mg/kg per day.

4.4.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g. granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

4.4.2 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.4.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection (reconstitutable powders), suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

4.4.4 Transdermal and Topical Dosage Forms

Transdermal and topical dosage forms of the invention include, but are not limited to, creams, lotions, ointments, gels, solutions, emulsions, suspensions, or other forms known to one of skill in the art. See, e.g., *Remington's Pharmaceutical Sciences,* 18th eds., Mack Publishing, Easton Pa. (1990); and *Introduction to Pharmaceutical Dosage Forms,* 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences,* 118th eds., Mack Publishing, Easton Pa. (1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.4.5 Mucosal Dosage Forms

Mucosal dosage forms of the invention include, but are not limited to, ophthalmic solutions, sprays and aerosols, or other forms known to one of skill in the art. See, e.g., *Remington's Pharmaceutical Sciences,* 18th eds., Mack Publishing, Easton Pa. (1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

Clofarabine may also be administered directly to the lung by inhalation. For administration by inhalation, clofarabine can be conveniently delivered to the lung by a number of different devices. For example, a Metered Dose Inhaler ("MDI") which utilizes canisters that contain a suitable low boiling propellant, e.g. dichlorodifluoromethane, trichlorofluoromethane, dichlorotetrafluoroethane, carbon dioxide or other suitable gas can be used to deliver a compound of formula I directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer a compound of formula I to the lung (See, e.g., Raleigh et al., Proc. Amer. Assoc. Cancer Research Annual Meeting, 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver clofarabine to the lung is a liquid spray device supplied, for example, by Aradigm Corporation. Liquid spray systems use extremely small nozzle holes to aerosolize liquid drug formulations that can then be directly inhaled into the lung.

In a preferred embodiment, a nebulizer device is used to deliver clofarabine to the lung. Nebulizers create aerosols from liquid drug formulations by using, for example, ultrasonic energy to form fine particles that can be readily inhaled (See e.g. Verschoyle et al., British J Cancer, 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics. Inhaled compound of formula I, delivered by nebulizer devices, is currently under investigation as a treatment for aerodigestive cancer (Engelke et al., Poster 342 at American Association of Cancer Research, San Francisco, Calif., Apr. 1-5, 2000) and lung cancer (Dahl et al., Poster 524 at American Association of Cancer Research, San Francisco, Calif., Apr. 1-5, 2000).

In a particularly preferred embodiment, an electrohydrodynamic ("EHD") aerosol device is used to deliver clofarabine to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the compound of formula I formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of clofarabine will be known to the skilled artisan and are within the scope of the invention.

Liquid drug formulations suitable for use with nebulizers and liquid spray devices and EHD aerosol devices will typically include a compound of formula I with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of clofarabine. Preferably, this material is liquid such as an alcohol, glycol, polyglycol or a fatty acid. Other methods of formulating liquid drug solutions or suspension suitable for use in aerosol devices are known to those of skill in the art (See, e.g., Biesalski, U.S. Pat. Nos. 5,112,598; Biesalski, 5,556,611, which are herein incorporated by reference) A compound of formula I can also be formulated in rectal or vaginal compositions such as suppositories or retention enemas, e.g., containing conventional suppository bases such as cocoa butter or other glycerides.

In addition to the formulations described previously, clofarabine can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver clofarabine. Certain organic solvents such as dimethylsulfoxide can also be employed, although usually at the cost of greater toxicity. A compound of formula I can also be delivered in a controlled release system. In one embodiment, a pump can be used (Sefton, CRC Crit. Ref Biomed Eng., 1987, 14, 201; Buchwald et al., Surgery, 1980, 88, 507; Saudek et al., N. Engl. J. Med, 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 3 Macromol. Sci. Rev. Macromol. Chem., 1983, 23, 61; see also Levy et al., Science 1985, 228, 190; During et al., Arm. Neurol., 1989, 25, 351; Howard et al., 1989, J. Neurosurg. 71, 105). In yet another embodiment, a controlled-release system can be placed in proximity of the target of the compounds of the invention, e.g., the lung, thus requiring only a fraction of the systemic dose (see, e.g., Goodson, in Medical Applications of Controlled Release, supra, vol. 2, pp. 115 (1984)). Other controlled-release system can be used (see e.g. Langer, Science, 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., *Remington's Pharmaceutical Sciences,* 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

This and other novel and unexpected advantages of the invention are further illustrated by the following non-limiting examples.

5. EXAMPLES

5.1 Example 1

Parenteral Dosage Formulation

Clofarabine, 9.86 g, is wetted/partially dissolved with 600 mL of a 9:1 mixture of tertiary butanol and Water for Injection USP which is pre-cooled to 5° C. Once the drug powder is completely wetted, dissolution is completed by the addition of 600 mL of a 1:9 mixture of tertiary butanol and Water for Injection and 766 mL of a 1:1 mixture of tertiary butanol and Water for Injection which likewise is pre-cooled to 5° C. thereby making the final solution a 1:1 mixture. The dissolution is carried out under protection from light.

The solution formed above is promptly lyophilized in a Virtis INOTOP lyophilizer at −16° C. under light protectant conditions over a period of 48 hours. The resultant lyophilized product (lyophile) is then further dried at 15° C. under high vacuum for 48 hours. No detectable degradation of the drug is observed during these procedures. The lyophile is packaged under sterile conditions into 30 mL vials, each containing 50 mg of drug, 50 mg of mannitol and sodium hydroxide to adjust the pH to 7.7 and standard excess to allow for vial/needle/syringe loss.

The lyophile is reconstituted with 2 mL of Water for Injection USP, which typically will be supplied with the drug in a separate vial, to achieve a final drug concentration of 25 mg/mL.

5.2 Example 2:25 Mg Dosage Capsule

Table 1 illustrates a batch formulation and a single dose unit formulation containing 25 mg of Clofarabine.

TABLE 1

Formulation for 25 mg tablet

| Material | Percent by Weight | Quantity (mg/tablet) | Quantity (kg/batch) |
|---|---|---|---|
| Clofarabine | 40% | 25.00 | 20.00 |
| Microcrystalline Cellulose, NF | 53.5% | 33.44 | 26.75 |
| Pluronic F-68 Surfactant | 4.0% | 2.50 | 2.00 |
| Croscarmellose Sodium Type A, NF | 2.0% | 1.25 | 1.00 |
| Magnesium Stearate, NF | 0.5% | 0.3125 | 0.25 |
| Total | 100.0% | 62.50 mg | 50.00 kg |

The microcrystalline cellulose, croscarmellose sodium, and Clofarabine components are passed through a #30 mesh screen (about 430μ to about 655μ). The Pluronic F-68® (manufactured by JRH Biosciences, Inc. of Lenexa, Kans.) surfactant is passed through a #20 mesh screen (about 457μ to about 1041μ). The Pluronic F-68® surfactant and 0.5 kgs of croscarmellose sodium are loaded into a 16 qt. twin shell tumble blender and are mixed for about 5 minutes. The mix is then transferred to a 3 cubic foot twin shell tumble blender where the microcrystalline cellulose is added and blended for about 5 minutes. The thalidomide is added and blended for an additional 25 minutes. This pre-blend is passed through a roller compactor with a hammer mill attached at the discharge of the roller compactor and moved back to the tumble blender. The remaining croscarmellose sodium and magnesium stearate is added to the tumble blender and blended for about 3 minutes. The final mixture is compressed on a rotary tablet press with 62.5 mg per tablet (800,000 tablet batch size).

5.3 Example 3

50 Mg Dosage Capsule

Table 2 illustrates a batch formulation and a single dose unit formulation containing 50 mg of Clofarabine.

TABLE 2

Formulation for 50 mg tablet

| Material | Percent by Weight | Quantity (mg/tablet) | Quantity (kg/batch) |
|---|---|---|---|
| Clofarabine | 40% | 50.00 | 20.00 |
| Microcrystalline Cellulose, NF | 53.5% | 66.875 | 26.75 |
| Pluronic F-68 Surfactant | 4.0% | 5.00 | 2.00 |
| Croscarmellose Sodium Type A, NF | 2.0% | 2.50 | 1.00 |
| Magnesium Stearate, NF | 0.5% | 0.625 | 0.25 |
| Total | 100.0% | 125.00 mg | 50.00 kg |

The microcrystalline cellulose, croscarmellose sodium, and Clofarabine components are passed through a #30 mesh screen (about 430μ to about 655μ). The Pluronic F-68® (manufactured by JRH Biosciences, Inc. of Lenexa, Kans.) surfactant is passed through a #20 mesh screen (about 457μ to about 1041μ). The Pluronic F-680® surfactant and 0.5 kgs of croscarmellose sodium are loaded into a 16 qt. twin shell tumble blender and are mixed for about 5 minutes. The mix is then transferred to a 3 cubic foot twin shell tumble blender where the microcrystalline cellulose is added and blended for about 5 minutes. The thalidomide is added and blended for an additional 25 minutes. This pre-blend is passed through a roller compactor with a hammer mill attached at the discharge of the roller compactor and moved back to the tumble blender. The remaining croscarmellose sodium and magnesium stearate is added to the tumble blender and blended for about 3 minutes. The final mixture is compressed on a rotary tablet press with 125 mg per tablet (400,000 tablet batch size).

5.4 Example 4

200 Mg Dosage Capsule

Table 3 illustrates a batch formulation and single dosage formulation for a 200 mg Clofarabine single dose unit, i.e., about 40 percent by weight.

TABLE 3

Formulation for 200 mg capsule

| Material | Percent By Weigh | Quantity (mg/tablet) | Quantity (kg/batch) |
|---|---|---|---|
| Clofarabine | 40.0% | 200 mg | 16.80 kg |
| Pregelatinized Corn Starch, NF5 | 9.5% | 297.5 mg | 24.99 kg |
| Magnesium Stearate | 0.5% | 2.5 mg | 0.21 kg |
| Total | 100.0% | 500 mg | 42.00 kg |

The pregelatinized corn starch (SPRESS B-820) and 3-[2-(3'-methyl-biphen-4-yloxy)-acetylamino]-benzoic acid components are passed through a 710 μm screen and then are loaded into a Diffusion Mixer with a baffle insert and blended for 15 minutes. The magnesium stearate is passed through a 210 μL m screen and is added to the Diffusion Mixer. The blend is then encapsulated in a size #0 capsule, 500 mg per capsule (8400 capsule batch size) using a Dosator type capsule filling machine.

5.5 Example 5

100 Mg Oral Dosage Form

Table 4 illustrates a batch formulation and a single dose unit formulation containing 100 mg of Clofarabine.

TABLE 4

Formulation for 100 mg tablet

| Material | Percent by Weight | Quantity (mg/tablet) | Quantity (kg/batch) |
|---|---|---|---|
| Clofarabine | 40% | 100.00 | 20.00 |
| Microcrystalline Cellulose, NF | 53.5% | 133.75 | 26.75 |
| Pluronic F-68 Surfactant | 4.0% | 10.00 | 2.00 |
| Croscarmellose Sodium Type A, NF | 2.0% | 5.00 | 1.00 |
| Magnesium Stearate, NF | 0.5% | 1.25 | 0.25 |
| Total | 100.0% | 250.00 mg | 50.00 kg |

The microcrystalline cellulose, croscarmellose sodium, and Clofarabine components are passed through a #30 mesh screen (about 430μ to about 655μ). The Pluronic F-68® (manufactured by JRH Biosciences, Inc. of Lenexa, Kans.) surfactant is passed through a #20 mesh screen (about 457μ to about 1041μ). The Pluronic F-68® surfactant and 0.5 kgs of croscarmellose sodium are loaded into a 16 qt. twin shell tumble blender and are mixed for about 5 minutes. The mix is then transferred to a 3 cubic foot twin shell tumble blender where the microcrystalline cellulose is added and blended for about 5 minutes. The thalidomide is added and blended for an additional 25 minutes. This pre-blend is passed through a roller compactor with a hammer mill attached at the discharge of the roller compactor and moved back to the tumble blender. The remaining croscarmellose sodium and magnesium stearate is added to the tumble blender and blended for about 3 minutes. The final mixture is compressed on a rotary tablet press with 250 mg per tablet (200,000 tablet batch size).

5.6 Example 6

Aerosol Dosage Form

A concentrate is prepared by combining Clofarabine, and a 12.6 kg portion of the trichloromonofluoromethane in a sealed stainless steel vessel equipped with a high shear mixer. Mixing is carried out for about 20 minutes. The bulk suspension is then prepared in the sealed vessel by combining the concentrate with the balance of the propellants in a bulk product tank that is temperature controlled to 21° to 27° C. and pressure controlled to 2.8 to 4.0 BAR. 17 ml aerosol containers which have a metered valve which is designed to provide 100 inhalations of the composition of the invention. Each container is provided with the following:

| | |
|---|---|
| Clofarabine | 0.0141 g |
| trichloromonofluoromethane | 1.6939 g |
| dichlorodifluoromethane | 3.7154 g |
| dichlorotetrafluoroethane | 1.5766 g |
| total | 7.0000 g |

While the invention has been described with respect to the particular embodiments, it will be apparent to those skilled in the art that various changes and modifications may be made without departing from the spirit and scope of the invention as defined in the claims. Such modifications are also intended to fall within the scope of the appended claims.

The invention claimed is:

1. A method of treating multiple sclerosis which comprises administering to a patient from about 1.25 mg/kg/day to about 80 mg/kg/day of clofarabine or a pharmaceutically acceptable salt, stereoisomer, solvate, hydrate, clathrate, prodrug or metabolite thereof.

2. The method of claim 1 which comprises administering from about 50 mg/kg/day to about 75 mg/kg/day of clofarabine or a pharmaceutically acceptable salt, stereoisomer, solvate, hydrate, clathrate, prodrug or metabolite thereof.

3. The method of claim 1 which comprises administering from about 20 mg/kg/day to about 60 mg/kg/day of clofarabine or a pharmaceutically acceptable salt, stereoisomer, solvate, hydrate, clathrate, prodrug or metabolite thereof.

4. The method of claim 1 which comprises administering from about 40 mg/kg/day to about 50 mg/kg/day of clofarabine or a pharmaceutically acceptable salt, stereoisomer, solvate, hydrate, clathrate, prodrug or metabolite thereof.

5. The method of claim 1 wherein the therapeutically or prophylactively effective amount of clofarabine is administered parenterally.

6. The method of claim 1 wherein the therapeutically or prophylactively effective amount of clofarabine is administered orally.

7. A method of treating psoriasis which comprises administering to a patient having psoriasis a therapeutically effective amount of clofarabine or a pharmaceutically acceptable salt, stereoisomer or solvate thereof.

8. The method of claim 7, wherein clofarabine or a pharmaceutically acceptable salt, stereoisomer or solvate thereof is administered in a tablet.

9. The method of claim 8, wherein the tablet comprises about 25 mg of clofarabine.

10. The method of claim 8, wherein the tablet comprises about 50 mg of clofarabine.

11. The method of claim 8, wherein the tablet comprises about 100 mg of clofarabine.

12. The method of claim 8, wherein the tablet comprises about 200 mg of clofarabine.

13. The method of claim 7 wherein the therapeutically or prophylactically effective amount of clofarabine is from about 5 mg/kg/day to about 75 mg/kg/day.

14. The method of claim 7 wherein the therapeutically or prophylactically effective amount of clofarabine is from about 20 mg/kg/day to about 60 mg/kg/day.

15. The method of claim 7 wherein the therapeutically or prophylactically effective amount of clofarabine is from about 40 mg/kg/day to about 50 mg/kg/day.

16. The method of claim 7 further comprising the administration of an additional therapeutic agent.

17. The method of claim 16 wherein the additional therapeutic agent is an antibiotic, an antiemetic agent, an antidepressant, and antifungal agent, an anti-inflammatory agent, an antiviral agent, an immunomodulatory agent, a β-interferon, an alkylating agent, a hormone or a cytokine.

18. The method of claim 7, wherein clofarabine is administered as a pharmaceutically acceptable salt.

19. The method of claim 7, wherein clofarabine is administered as a free base.

20. The method of claim 17, wherein the immunomodulatory agent is selected from the group consisting of methothrexate, leflunomide, cyclophosphamide, cytoxan, lmmuran, cyclosporine A, minocycline, azathioprine, antibiotics, tacrolimus, methylprednisolone, corticosteroids, steriods, mycophenolate mofetil, rapamycin, sirolimus, mizoribine, deoxyspergualin, brequinar, malononitriloamindes, T cell receptor modulators, and cytokine receptor modulators.

* * * * *